United States Patent [19]

Leyse

[11] Patent Number: 5,621,161

[45] Date of Patent: Apr. 15, 1997

[54] METHOD FOR MONITORING FOR THE PRESENCE OF DISSOLVED GAS IN A FLUID UNDER PRESSURE

[76] Inventor: Robert H. Leyse, 12136 Brookglen Dr., Saratoga, Calif. 95070

[21] Appl. No.: 419,700

[22] Filed: Apr. 11, 1995

[51] Int. Cl.⁶ .......................... G01N 7/00; G01N 33/497
[52] U.S. Cl. .......................... 73/19.01; 73/19.1; 73/31.05
[58] Field of Search .................................. 73/19.01, 19.1, 73/23.31, 23.42, 335.02, 335.05, 31.04, 31.05

[56] References Cited

U.S. PATENT DOCUMENTS

| | | |
|---|---|---|
| 3,177,700 | 4/1965 | Sier . |
| 3,488,584 | 1/1970 | Ziniuk . |
| 3,746,980 | 7/1973 | Timrot et al. . |
| 3,786,345 | 1/1974 | Mikkelsen .................. 324/30 R |
| 3,944,824 | 3/1976 | Chagny et al. .................. 250/288 |
| 3,946,228 | 3/1976 | Biermann .................. 73/19.01 |
| 4,003,814 | 1/1977 | Tarassoff et al. . |
| 4,361,802 | 11/1982 | Luijpers . |
| 4,383,221 | 5/1983 | Morey . |
| 4,454,748 | 6/1984 | Terai et al. .................. 73/27 |
| 4,731,732 | 3/1988 | Warchol et al. .................. 364/510 |
| 4,924,695 | 3/1990 | Kolpak .................. 73/19.01 |
| 4,965,041 | 10/1990 | Becker . |
| 4,978,921 | 12/1990 | Indig . |
| 4,990,855 | 2/1991 | Niedarch et al. . |

Primary Examiner—Richard Chilcot
Assistant Examiner—Max H. Noori
Attorney, Agent, or Firm—William D. Hall

[57] ABSTRACT

An apparatus and method for determining the presence of dissolved gas in a fluid under pressure. A test cell capable of containing the pressurized fluid has a test instrument disposed therein. The test instrument has two platinum leads connected by a sensor element. The platinum leads are connected to an external source of electrical power. A thermocouple is mounted in the test instrument. The apparatus is calibrated using degassed, demineralized fluid at a known pressure by applying power to the platinum leads in a stepwise manner and recording the resistance of the sensor element versus applied power. The test cell is connected to fluid suspected of having gas dissolved therein and power is applied in a stepwise manner to the platinum leads. The power applied versus the resistance of the sensor element is recorded. A comparison between the power versus resistance for the degassed fluid and the suspect fluid discloses the presence of dissolved gas.

20 Claims, 3 Drawing Sheets

Fig.1
Fig.2
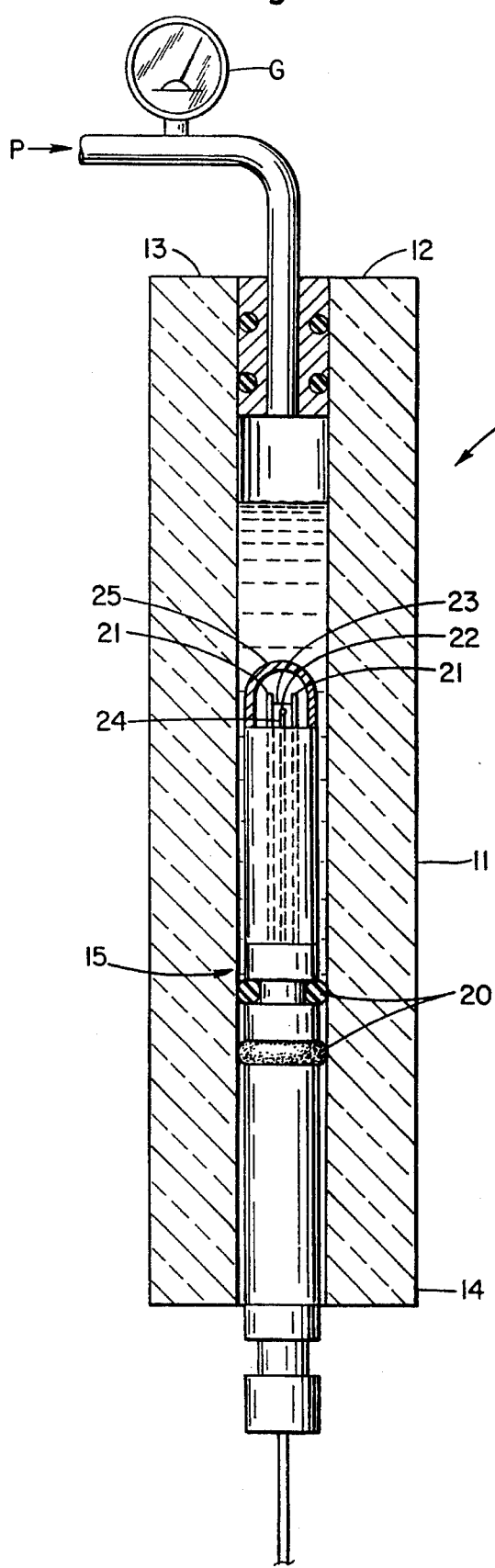
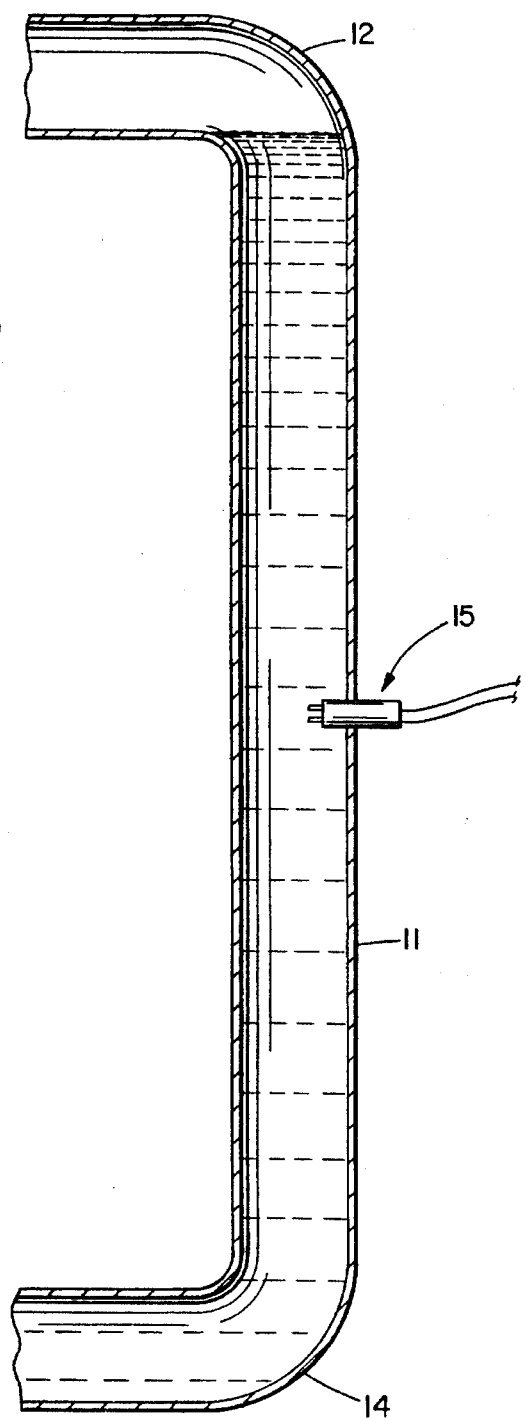

METHOD FOR MONITORING FOR THE PRESENCE OF DISSOLVED GAS IN A FLUID UNDER PRESSURE

The present invention relates to dissolved gases in fluids under pressure and, more particularly, to relating the electrical resistance of a sensor element to the presence of the dissolved gas.

BACKGROUND OF THE INVENTION

The presence of dissolved gas in fluid, such as water, under pressure can lead to unacceptable performance of certain support and monitoring equipment in industry. These factors are extremely important in nuclear power plants. In both pressurized water reactors and boiling water reactors, the presence of dissolved gas in reference level pipes for water level detectors leads to outgassing and degradation of calibration. In the case of the water-filled accumulators for an emergency core cooling system, called upper head injection, the presence of substantial amounts of dissolved gas (such as hydrogen and nitrogen) degrades the ability of the system to function and provide emergency core cooling. Dissolved gas is released during rapid pressure reductions which results in expulsion of fluid from reference pipes. This leads to erroneous vessel level readings at a time when there is a critical need for accurate level measurement.

A method and apparatus for measuring the gas content of metal samples is disclosed in U.S. Pat. No. 3,177,700 issued to Sier. A predetermined quantity of inert gas is present and a katarmeter is used to measure the amount of liberated gas using a Wheatstone bridge circuit.

U.S. Pat. No. 4,965,041 issued to Becker discloses an instrument for monitoring the cooling conditions of the reactor core of a nuclear reactor. An electrical resistor is heated and the temperature of the resistor is monitored.

U.S. Pat. No. 3,488,584 issued to Ziniuk discloses a high frequency bridge including a sensing probe disposed in a flowing liquid metal and a second probe in a reference sample of known purity. Thus any difference in electrical resistivity is due to a difference in contamination.

None of these references are directed toward monitoring dissolved gas in a fluid such as water. A need for a simple rapid responding device for monitoring the presence of dissolved gas in a fluid is needed for applications such as in nuclear reactors.

SUMMARY OF THE INVENTION

Accordingly, it is an object of the present invention to provide an apparatus and method which can be used to monitor fluids for the presence of dissolved gas in the fluid.

It is another object of the present invention to provide an apparatus having a sensing element to which power is applied in a continuously increasing manner and in which the resistance of the sensing element is related to the presence of dissolved gas in the water in which the sensing element is immersed.

In accordance with the teachings of the present invention, there is disclosed herewith an apparatus for determining the presence of dissolved gas in water under pressure. The apparatus has a test cell capable of containing water and withstanding pressure of at least 2500 psi. The cell has an upper end and a lower end. Means are provided for introducing pressure into the upper end of the test cell. A test instrument having a tip is disposed in the test cell. The test instrument has a pair of spaced-apart platinum wires mounted in the tip thereof. A sensor element is connected to the pair of platinum wires and a thermocouple is mounted in the test instrument. Means are provided for applying electrical power through the platinum wires to the sensor element. Means are provided for measuring the electrical resistance of the sensor element, wherein the electrical resistance of the sensor is a function of the dissolved gas in the water.

A method is disclosed for determining the presence of dissolved gas in a fluid under pressure. The method provides a test cell capable of containing water and withstanding pressure of at least 2500 psi. A test instrument is disposed in the test cell, the test instrument having a sensor element to which electrical power can be applied. Means are provided for measuring the electrical resistance of the sensor element. The sensor element is calibrated at a measured temperature using degassed, demineralized fluid having a known resistance. The power applied versus the resistance of the sensor element is recorded to determine the change of resistance of the sensor element. The test cell is allowed to stabilize with a test fluid which is under a gas at a known pressure such that gas dissolves in the test fluid. The temperature of the test fluid containing dissolved gas in the test instrument is measured. The electrical power applied to the sensor element is increased in a continuous manner and the power applied is continuously recorded. The electrical resistance of the sensor element is continuously recorded during the increase in electrical power. The power applied versus the resistance of the sensor element is recorded to determine the change of resistance of the sensor element when immersed in the test fluid containing dissolved gas. The records showing the change of resistance of the sensor element for degassed fluid and for test fluid containing dissolved gas are compared and the presence of dissolved gas in the test fluid is determined.

These and other objects of the present invention will become apparent from a reading of the following specification, taken in conjunction with the enclosed drawings.

BRIEF DESCRIPTION OF THE DRAWINGS

FIG. 1 is a side elevation view of the apparatus of the present invention installed in a test cell for calibration and showing the pair of platinum wires, the sensor element and the thermocouple.

FIG. 2 is a side elevation view of the test instrument in a typical application.

DESCRIPTION OF THE PREFERRED EMBODIMENT

Figure 3:
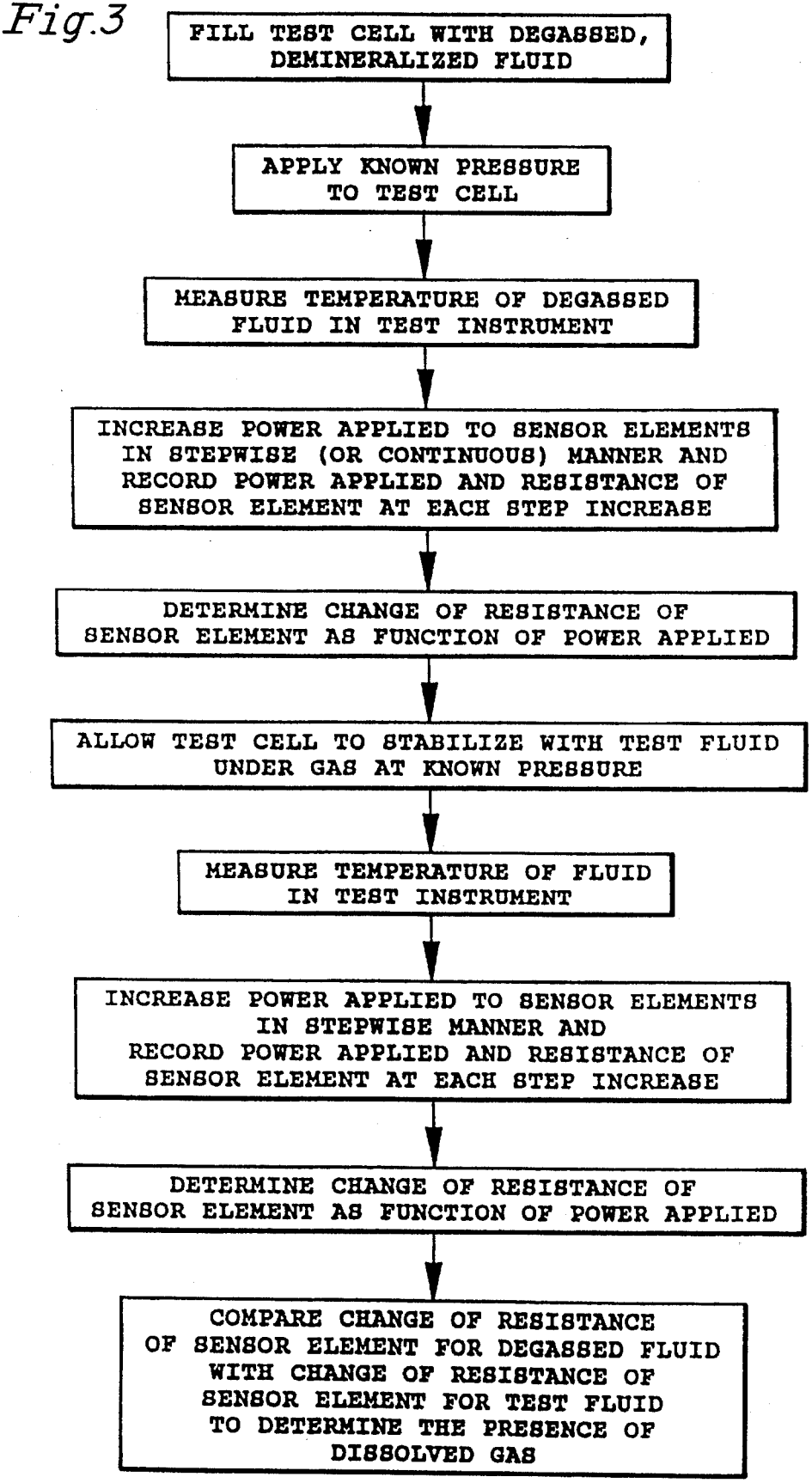
FIG. 3 is a diagram showing the method of calibration of the present invention.

Referring to FIGS. 1 and 2, the apparatus 10 of the present invention has a test cell 11 which is a hollow tube, open at both ends with walls capable of withstanding pressures of at least 2500 psi. The test cell may be glass or other material and, in situations where pressures up to 4000 psi may be encountered, the test cell may be formed of metal such as stainless steel. In a typical situation, the test cell has an internal cross section of approximately 0.28 inches and a length of approximately 10 inches, although test cells of differing configurations and dimensions may be used.

The top 12 of the test cell 11 has means formed thereon for connection to a source of pressure P such as the ambient pressurized system in which the apparatus 10 is used. The means may be a fitting 13 or other connector. For calibration purposes it is preferred that the test instrument 15 be mounted in the bottom 14 of the test cell 11. The mounting is able to withstand pressure and is water tight to permit filling of the test cell with water.

The test instrument 15 is preferably in the shape of a probe which can be inserted into the test cell 11. Improved sealing of the test instrument 15 in the cell may be achieved by 0 rings 20 about the test instrument 15. However, other sealing means may be used and the test instrument may have a shape which is not cylindrical. A pair of spaced-apart platinum leads 21 are mounted near the first end of the test instrument 15. The platinum leads 21 preferably have a diameter of 0.015 inches and are isolated by a core preferably formed from magnesium oxide to serve as an insulator. The platinum leads 21 extend the length of the test instrument and means are provided to make electrical connections to the leads 21 at the second end of the test instrument 15 external of the test instrument for measurement purposes. A sensor element 23 is connected to each of the platinum leads 21 at the first end of the test instrument 15 so as to form a bridge therebetween. Preferably, the sensor element 23 is a platinum wire approximately 0.1 inch long having a diameter of approximately 0.0003 inches. A thermocouple 24 is mounted in the test instrument 15 adjacent to the sensor element 23 to monitor the water temperature. Preferably a type K thermocouple is used. A cap 25 may be formed on the tip of the test instrument 15 to cover the platinum leads 21, the sensor element 23 and the thermocouple 24. The cap 25 may be in the form of a bell jar. Optionally, the cap 25 may be vented.

For calibration (FIG. 3), the test cell 11 is evacuated to a vacuum of less than 0.01 inch mercury as measured with a gauge G, and then backfilled with degassed, demineralized water. The system is pressurized to test pressure with a hydrostatic test pump or similar means. The bulk water temperature is measured with the type K thermocouple 24. Testing then consists of increasing the power continuously and recording the applied voltage and electrical current continuously to determine the power (multiply voltage times current) and the resistance of the platinum sensor element 23 at each power (divide voltage by current). In this manner, a power-resistance characteristic is obtained for the sensor element 23 in the fluid. In this manner, the test cell 11 is calibrated using degassed fluid. In a typical application, several solutions are prepared, each having a known amount of gas dissolved therein. The procedure is repeated for at least two pressures (i.e., 100 psi and 2200 psi). In this manner, a calibration of the test cell 11 may be obtained. This permits determining the presence of dissolved gas at various pressures since the solubility of a gas increases with increased pressure. The calibrated device 10 is mounted in the equipment in which the pressurized fluid is to be monitored. The temperature of the fluid is measured because the resistance of the sensor element with no applied power is a function of the temperature of the fluid in which the sensor is immersed. The power is increased continuously and the voltage and amperage are recorded continuously.

The resistance of the sensor element 23 is recorded. The change in resistance of the sensor element 23 versus power is compared with the calibrated data and the presence of dissolved gas is determined.

Figure 4:
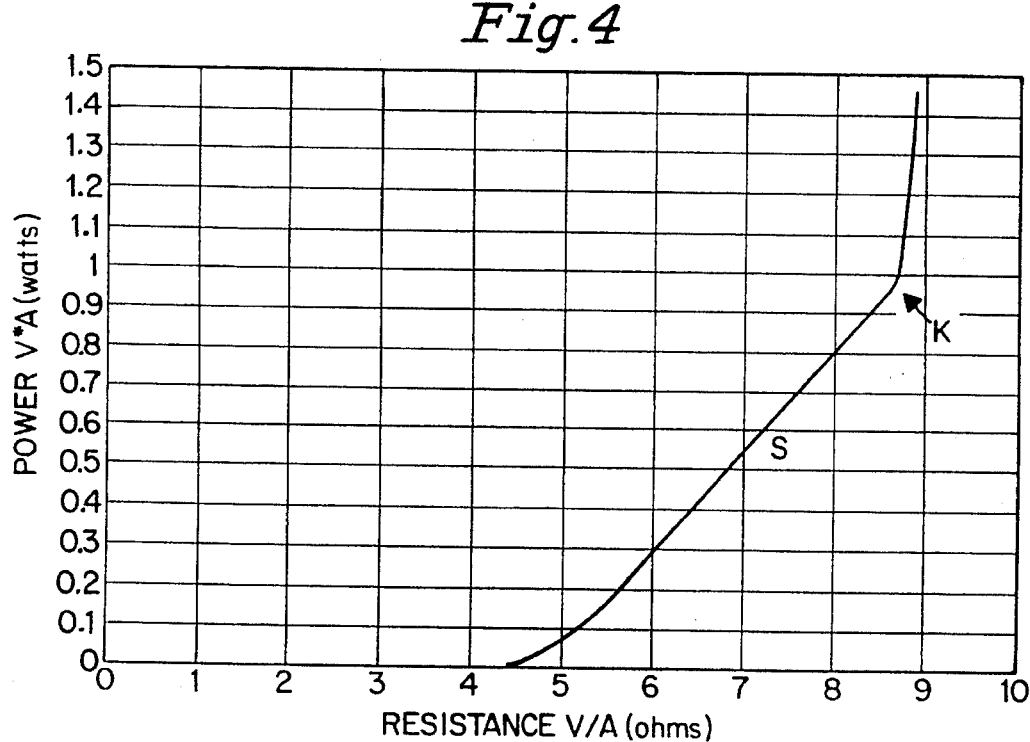
FIG. 4 is a plot of power versus resistance of the sensor element when immersed in degassed water at approximately a temperature of 70° F. and a pressure of 1000 pounds per square inch.
Figure 5:
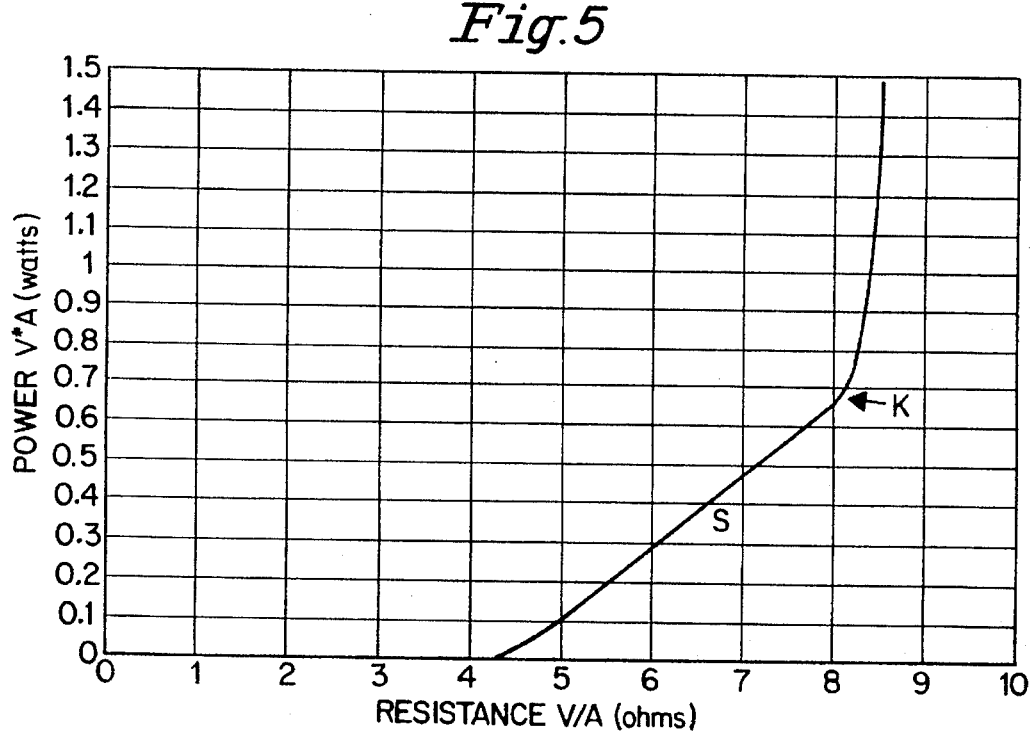
FIG. 5 is a plot of power versus resistance of the sensor element when immersed in water saturated with nitrogen at approximately a temperature of 70° F. and a pressure of 1000 pounds per square inch.

The plot of power applied versus resistance of the sensor element when immersed in degassed water at approximately 1000 psi is shown in FIG. 4. A corresponding plot of water saturated with nitrogen at approximately 1000 psi shown in FIG. 5 reveals several aspects which quantify the presence of dissolved nitrogen in the nitrogen saturated water relative to the degassed water. Each curve has a region of linear increasing slope S and a knee K at which the slope abruptly increases. With degassed water, the linear slope S is 0.26 watts/ohm while for water saturated with nitrogen the slope S is 0.19 watts/ohm. With degassed water, the coordinates of the knee K are 8.7 ohms and 0.97 watts while with water saturated with nitrogen, the coordinates of the knee K are 8.0 ohms and 0.66 watts. Similar calibrations may be produced for intermediate concentrations of dissolved nitrogen.

The device may be used with fluids in which various gases are dissolved under pressure and is not limited to hydrogen or nitrogen, nor must the fluid be saturated with the gas. The measurement of resistance compared to power is indicative of the presence of dissolved gas in the fluid.

In a particularly preferred procedure, the power is continuously increased over a period of 5 seconds and then turned off. The data is recorded and the comparative curves are plotted. Voltage and amperage are recorded at each step. The slope S of the region of linear increasing slope as well as the power at the knee K where the slope abruptly increases, are not extremely temperature dependent or pressure dependent over nominal ranges. The initial value of the resistance of the sensor element 23, while the applied power is very low, is a function of the fluid temperature. For most field applications of the apparatus, the main function of the type K thermocouple 24 is to check on the status of the sensor element 23; that is, the value of the resistance of the sensor element 23 at low applied powers should be consistent with the temperature indicated by the type K thermocouple 24. For field applications in which the fluid temperature will not change over a relatively wide range, it is not necessary to include the type K thermocouple 24.

The device 10 of the present invention is very compact and can easily be inserted within pipes in industrial applications such as the reference level pipes in a nuclear reactor installation. The device 10 requires no special equipment for measuring the data produced; commercially available ammeters, voltmeters and ohmmeters can be used. There is no need for sampling lines with the attendant complexity and risk of loss of the sample character.

Obviously, many modifications may be made without departing from the basic spirit of the present invention. Accordingly, it will be appreciated by those skilled in the art that within the scope of the appended claims, the invention may be practiced other than has been specifically described herein.

I claim:

1. A method for determining the presence of dissolved gas in a fluid under pressure comprising the steps of:

providing a test cell capable of containing fluid and withstanding pressure of at least 2500 psi, providing a test instrument disposed in the fluid, the test instrument having a sensor element to which electrical power can be applied, providing means for measuring the electrical resistance of the sensor element, calibrating the sensor element at a measured temperature and a measured pressure using gas-free fluid, recording the power applied to the sensor element versus the resistance of the sensor element to determine the power-resistance characteristic of the sensor element in the gas-free degassed, demineralized fluid, locating said sensor element within the fluid within the process equipment in which the presence of dissolved gas in the fluid is to be determined, measuring the temperature and the pressure of the fluid within the process equipment, increasing the electrical power applied to the sensor element in a continuous manner and recording the power, measuring the electrical resistance of the sensor element continuously with the increase in electrical power, recording the power applied to the sensor element versus the resistance of the sensor element to determine the power-resistance characteristic for the sensor element in the fluid suspected of containing dissolved gas, comparing the recordings showing the power-resistance characteristics for the sensor element in the degassed fluid and for the sensor element in the fluid suspected of containing dissolved gas and determining the presence of dissolved gas in the suspect fluid.

2. The method of claim 1, wherein the power applied to the sensor element and the resistance of the sensor element is measured by continuously determining the voltage and electrical current applied.

3. The method of claim 1, wherein the manner of increasing the electrical power is continuous over a period of approximately 5 seconds and then turning off the power.

4. The method of claim 1, wherein the sensor element is further calibrated over a range of fixed temperatures and pressures.

5. A method for quantitatively determining the presence of dissolved gas in a fluid under pressure comprising the steps of:

providing a test cell capable of containing fluid, providing a test instrument disposed in the fluid, the test instrument having a sensor element to which electrical power can be applied, providing means for measuring the electrical resistance of the sensor element, calibrating the sensor element at a measured temperature and a measured pressure using degassed, demineralized fluid, recording the power applied versus the resistance of the sensor element to determine the power-resistance characteristic of the sensor element in the degassed, demineralized fluid, calibrating the sensor element at the measured temperature and the measured pressure using the fluid having a known quantity of gas dissolved therein, recording the power applied versus the resistance of the sensor element to determine the power-resistance characteristic of the sensor element in the fluid having a known quantity of gas dissolved therein, locating said sensor element within the fluid within the process equipment in which the quantity of dissolved gas in the fluid is to be determined, measuring the temperature and the pressure of the fluid within the process equipment, increasing the electrical power applied to the sensor element in a continuous manner and recording the power, measuring the electrical resistance of the sensor element continuously as the electrical power increases, recording the power applied to the sensor element versus the resistance of the sensor element to determine the power-resistance characteristic for the sensor element in the fluid suspected of containing dissolved gas, comparing the recordings showing the power-resistance characteristics for the sensor element in the degassed fluid, for the fluid with known gas and for fluid suspected of containing dissolved gas and determining the quantity of dissolved gas in the suspect fluid.

6. The method of claim 5, comprising calibrating the sensor element over a range of fixed temperatures, pressures and known quantities of gas dissolved in the fluid.

7. The method of determining whether a water-based fluid contains gas, comprising:

(a) providing a water-based fluid, (b) providing a resistor whose resistance may vary, (c) immersing the resistor in said water-based fluid, (d) applying a voltage across said resistor thereby passing an electric current through said resistor, and (e) determining from variations in at least one of said voltage and current whether there is gas in the water-based fluid.

8. The method of claim 7, in which said voltage and current applies power to said resistor, aid step (e) comprising varying said power while said determination is being made.

9. The method of claim 8, in which said step (e) includes varying said resistance while said determination is being made.

10. The method of claim 8, in which said step (e) includes varying both said power and said resistance as a part of said determination.

11. The method of claim 8, in which said step (e) includes increasing both said power and said resistance and making said determination based on changes in the relative rates at which said power and resistance increase.

12. The method of claim 8, in which said step (e) includes varying both the amount of said power and the amount of said resistance and making said determination based on the rate of change in the amounts of said power and said resistance.

13. The method of claim 8, in which the amounts of said power and said resistance are varied, plotting a curve having two coordinates, with said curve showing the variations in power along one of said coordinates and the variation in said resistance along the other of said coordinates, and making said determination based on the shape of said curve.

14. The method of claim 7, in which said determination comprises determining that there is at least a predetermined amount of gas in said water-based fluid.

15. The method of claim 7, in which said step of providing a resistor comprises providing a platinum wire.

16. The method of claim 7, wherein said step of immersing the resistor in the water-based fluid comprises immersing the resistor in a sample of the water-based fluid that is not moving.

17. The method of claim 7, comprising, step (e) including multiplying said voltage by the current, to determine power, dividing said current by said voltage to determine the amount of resistance, and determining the presence of gas in said fluid by comparing variations in said power with variations in said amount of resistance.

18. The method of claim 7, wherein said step (e), comprises:

measuring said voltage and said current, and using such measurements to determine whether there is gas in said water-based fluid.

19. The method of claim 7, in which said step (e) includes:

determining the amount of power fed to said resistor as well as the amount of said resistance, and determining from said amounts whether there is gas in the water-based fluid.

20. The method of claim 7, comprising:

using said voltage and current to determine the amount of power fed to said resistor and the amount of the resistance of said resistor, and using said amounts for determining whether there is gas in the water-based fluid.

* * * * *